United States Patent [19]

Billmers et al.

[11] Patent Number: 5,776,476

[45] Date of Patent: Jul. 7, 1998

[54] COSMETIC COMPOSITIONS CONTAINING HYDROPHOBIC STARCH DERIVATIVES

[75] Inventors: Robert L. Billmers, Stockton; Daniel B. Solarek, Belle Mead; Maria Tolchinsky, Piscataway; Donna L. Ronco, Oxford; Joseph Pasapane, Morristown, all of N.J.

[73] Assignee: National Starch and Chemical Investment Holding Corporation, Wilmington, Del.

[21] Appl. No.: 808,730

[22] Filed: Feb. 28, 1997

[51] Int. Cl.$^6$ .................................................. A61K 7/48
[52] U.S. Cl. ............... 424/401; 424/47; 424/69; 424/707; 514/60; 514/844; 514/845; 514/846
[58] Field of Search .......................... 424/401, 707, 424/47, 69; 514/844, 845, 846, 60

[56] References Cited

U.S. PATENT DOCUMENTS

| | | | |
|---|---|---|---|
| 2,613,206 | 10/1952 | Caldwell | 260/233.5 |
| 2,661,349 | 12/1953 | Caldwell et al. | 260/224 |
| 3,852,475 | 12/1974 | Tarangul | 424/361 |
| 4,894,222 | 1/1990 | Matravera | 424/59 |
| 4,994,264 | 2/1991 | Verdon et al. | 424/63 |
| 5,013,764 | 5/1991 | Tubesing et al. | 514/772 |
| 5,407,678 | 4/1995 | Rose et al. | 424/401 |

OTHER PUBLICATIONS

R. L. Whistler et al., "Starch: Chemistry and Technology", Second Edition, pp. 341–343.

O. Wurzburg, "Modified Starches: Properties and Uses", 1986, Chapter 9, pp. 131–147.

*Primary Examiner*—Jyothsan Venkat
*Attorney, Agent, or Firm*—Eugene Zagarella, Jr.

[57] ABSTRACT

Cosmetic compositions useful in skin care are provided containing an effective aesthetic enhancing amount of calcium salt starch derivatives having the following formula:

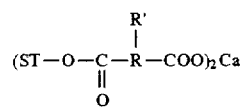

where ST is the starch base material, R is a dimethylene group and R' is a substituent hydrocarbon group having 10 to 16 carbon atoms.

12 Claims, No Drawings

COSMETIC COMPOSITIONS CONTAINING HYDROPHOBIC STARCH DERIVATIVES

BACKGROUND OF THE INVENTION

This invention relates to cosmetic compositions used in skin care and comprising selected hydrophobic starch derivatives as an aesthetic enhancer and lubricating powder.

The preparation of starch derivatives and especially hydrophobic starch derivatives is well known as described in U.S. Pat. No. 2,661,349 issued Dec. 1, 1953 to C. Caldwell et al. and also in "Starch: Chemistry and Technology", second edition, edited by R. L. Whistler et al., 1984, pp. 341–343 and "Modified Starches: Properties and Uses", edited by O. Wurzburg, 1986, Chapter 9, p. 131–147. Free flowing, hydrophobic metal salts of modified starches are further disclosed in U.S. Pat. No. 2,613,206 issued Oct. 7, 1952 to C. Caldwell et al.

Over the years, starch octenylsuccinate derivative have been used in a variety of industrial, food, pharmaceutical and cosmetic applications because of their advantageous property attributes, particularly the ability to stabilize emulsions. Aluminum starch octenylsuccinate (OSA), a hydrophobic starch with good free flow and water repellant properties has been used in a number of different applications. Exemplary disclosures showing aluminum starch octenylsuccinates can be found in U.S. Pat. No. 5,013,763 issued May 7, 1991 to D. Tubesing et al. where the starch modified aluminum salt is used in skin preparations such as hand or body lotions and in U.S. Pat. No. 5,407,678 issued Apr. 18, 1995 to W. Rose et al. where it is used in petroleum jelly cosmetic compositions. Further disclosures of the aluminum salt of starch OSA are seen in U.S. Pat. No. 3,852,475 issued Dec. 3, 1974 to E. Tarangul where it is found in topical compositions containing petrolatum, in U.S. Pat. No. 4,994,264 issued Feb. 19, 1991 to D. Verdon et al. in press molded cosmetic compositions and in U.S. Pat. No. 4,894,222 issued Jan. 16, 1990 to P. Matravers where it is found in sunscreen preparations.

Despite the varied and significant use of the aluminum salt of starch modified OSA as described above, recent concern about the properties and effects of aluminum metal in some applications has resulted in an effort to find a replacement or substitute for it. The octenylsuccinate (OSA) starches of varying substitution and the salts, particularly calcium have been found deficient in one or more of the desired properties such as free flow and hydrophobicity.

SUMMARY OF THE INVENTION

Now it has been unexpectedly found that selected calcium salt starch derivatives provide good free flow and hydrophobic properties and also show a high degree of heat tolerance making them useful in cosmetic skin care compositions.

More particularly, this invention relates to cosmetic compositions containing an effective aesthetic enhancing amount of calcium salt starch derivatives having the following formula:

$$(ST-O-\underset{\underset{O}{\|}}{\underset{|}{C}}-R-COO)_2Ca \qquad (I)$$

where ST is the starch base material, R is a dimethylene group and R' is a substituent hydrocarbon group having 10 to 16 carbon atoms.

DETAILED DESCRIPTION OF THE INVENTION

The use of selected calcium salt starch derivatives in cosmetic skin care compositions in accordance with this invention provides an aluminum free starch product which exhibits good free flow and hydrophobic properties as well as increased heat stability. Additionally, the starch derivatives help provide the cosmetic composition with good aesthetic properties as well as feel (non-greasy).

The starch derivatives of this invention have the formula I, shown above where ST is the starch base material, R is dimethylene and R' is a hydrocarbon group having 10 to 16 and preferably 12 to 14 carbon atoms. The hydrocarbon or hydrophobic substituent group R' may be alkyl, alkenyl, aryl, aralkyl or aralkenyl, preferably alkyl or alkenyl and more preferably alkenyl. The amount of the derivative group bound to the starch, i.e.,

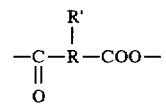

will be from about 3 to 25%, preferably from about 3.5 to 10% and more preferably from about 4 to 6% by weight based on the weight of dry starch The base starch material used herein may be any of several starches, native or converted. Such starches include those derived from any plant source including corn, potato, wheat, rice, sago, tapioca, waxy starches such as waxy maize, waxy potato and waxy rice, sorghum and high amylose starch such as high amylose corn, i.e., starch having at least 40% and more particularly at least 65% amylose content by weight. Starch flours may also be used. Also included are the conversion products derived from any of the former bases such as for example, dextrins prepared by hydrolytic action of acid and/or heat, fluidity or thin boiling starches prepared by enzyme conversion or mild acid hydrolysis, and oxidized starches prepared by treatment with oxidants such as sodium hypochlorite. Also included in the base starches are derivatized starches such as the hydroxy alkylated or etherified starches, e.g., hydroxypropyl, the esterified starches such as acetylated starch, cationic and anionic starches, and crosslinked starches such as those crosslinked with epichlorohydrin and phosphorus oxychloride.

While the preparation of starch derivatives including hydrophobic derivatives have been carried out for many years, as noted above, the ability to provide longer chain products such as those of this invention has not been easy. In some cases, particularly in aqueous systems, the starch and reagent will not react because of the limited solubility in water. An improved method for preparing the hydrophobic derivatives of this invention is disclosed in U.S. application Ser. No. 08/524,281, filed Sep. 6, 1995 wherein the starch and anhydride reagent are predispersed or intimately contacted by mixing at low acidic pH before being brought to reaction conditions. More particularly, this method involves reacting starch with an organic acid anhydride in an aqueous system wherein:

a) starch is slurried in water at an acid pH of less than 7.0;

b) an organic acid anhydride having the desired R and R' substituent groups (as in Formula I above) is added to the slurry;

c) the starch and anhydride reagent are intimately contacted by mixing to form a stable dispersion;

d) alkali material is added to the starch dispersion to adjust the pH to an alkaline pH of greater than 7.0 to initiate reaction and further adding alkali material to maintain that pH until the reaction is complete; and e) calcium salt added in either dry form or aqueous solution.

This method of preparing the hydrophobic starch derivatives of this invention is described in the '281 application noted above, which is incorporated herein by reference. Any calcium salt such as calcium chloride, calcium sulfate, calcium acetate and calcium hydroxide can be used to provide calcium metal and preferably calcium chloride or calcium sulfate. The salt can be added in any form and preferably in an aqueous solution and at a pH of less than 7.0. The amount of salt used is at least a stoichiometric amount and more particularly will be from about 2.5 to 5% by weight based on weight of dry starch.

The starch derivatives described above can be used in different cosmetic compositions such as skin care compositions where they provide free flow and hydrophobic properties and have heat stability and other rheological and aesthetic properties. The cosmetic skin care compositions of this invention may involve different media or systems and will comprise a suitable cosmetic vehicle or base for the composition. This vehicle may be an emulsion, an aqueous system, a solvent system or a combination of aqueous and solvent systems as well as anhydrous and powdered systems.

The emulsions are the preferred vehicle or base for the cosmetic compositions of this invention and products of this type include the skin care creams and lotions. These emulsions which comprise water-based and oil-based phases, may be oil-in-water emulsions having oil as the dispersed phase and water as the continuous phase or they may be water-in-oil emulsions with water dispersed in oil, which is the continuous phase. The oil phase, which may comprise from about 10 to 90% by weight of the composition, is typically made up of cosmetically acceptable or conventional oily substances that are soluble in this phase, such as oils, waxes and emulsifiers. Compounds which can be included in the oil phase are typically mineral, animal and vegetable oils and fats, synthetic esters, fatty acids, aliphatic alcohols, higher fatty alcohols, alkyl amines, waxes, so called mineral fats and oils, such as paraffin oil, petrolatum, ceresin, silicone oils and silicone fats. The water phase may comprise from about 10 to 90% by weight of the composition and this will include water and water soluble components such as alkalis, alkanolamines, polyhydric alcohols and preservatives. These emulsions include one or more emulsifiers which usually are contained in the oil phase but in some instances, depending on the type, may be in the water phase. Emulsifiers which can be used may be ionic or nonionic, are well known and constitute a large group of conventional and commercially available products. They are often characterized by their hydrophilic-lipophilic balance (HLB). Oil-in-water (O/W) emulsifying agents typically have an HLB of more than 6.0 and produce emulsions in which the continuous phase is hydrophilic and such emulsions are generally dispersible in water. Emulsifiers of this type include PEG 300 distearate, sorbitan monolaurate and triethanolamine stearate. Water-in-oil (W/O) emulsifiers usually have an HLB of less than 6.0, preferably below 5, and produce emulsions in which the continuous phase is lipophilic. Such emulsifiers include, lanolin alcohols, ethylene glycol monostearate, sorbitan mono-oleate and PEG 200 dilaurate. Emulsifiers with HLB's of between 5 and 7 may function as either W/O or O/W emulsifiers depending on how they are used.

The amount of emulsifier used in the emulsions of this invention can vary depending on the system and typically will be an effective emulsifying amount. More particularly, the amount of emulsifier can vary from about 0.1 to 20% by weight of the composition and preferably from about 0.2 to 10%.

Various other ingredients and additives may be included in one or both of the oil and water phases in the cosmetic skin care emulsions described above. This includes emollients, humectants, thickening agents, UV-light inhibitors, preservatives, pigments, dyes, colorants, alpha hydroxy acids, aesthetic enhancers such as perfumes and fragrances, film formers (water proofing agents), antiperspirants, deodorants, antiseptics, antifungal, antimicrobial and other medicaments and solvents. Effective amounts of one or more of these and other active and functional ingredients is generally used and this can total from about 0.1 to 25% by weight of the composition and more particularly from about 0.1 to 15%. The starch derivative will comprise from about 0.1 to 20% by weight, preferably 0.2 to 10% by weight of the emulsion system compositions.

Other cosmetic compositions using the selected starch derivatives in accordance with this invention involve aqueous or solvent systems wherein the added components are soluble or dispersible therein. The aqueous system will comprise the selected starch derivatives, additives and active and functional ingredients, optionally a propellant and the balance water. Generally, an aqueous system will comprise from about 10 to 99.8% by weight water, preferably 50 to 80%, from about 0.1 to 20% by weight of the starch derivative, preferably 0.2 to 10%, from about 0.1 to 25% by weight of additives and ingredients, preferably 0.1 to 15% and from about 0 to 50% by weight of propellant, preferably 0 to 30%. Compositions of this type include the topical sprays and products containing fragrances and antimicrobial agents.

The topical sprays include the aerosol sprays or products containing a propellant. While any of the known propellants may be used in the compositions of this invention, preferred propellants included the non-halogenated hydrocarbons, particularly the lower boiling hydrocarbons such as $C_3$–$C_6$ straight and branched chain hydrocarbons, i.e., propane, butane, isobutane and mixtures thereof. Other preferred propellants include the ethers, such as dimethyl ether, hydrofluorocarbon and the compressed gases such as $N_2$ and $CO_2$.

The use of a solvent system as the vehicle or base involves other cosmetic compositions containing the selected starch derivative. The solvent system will comprise the selected starch derivative, additives and active and functional ingredients, optionally a propellant and the balance solvent. The solvent may be any of the known organic solvents which may solubilize or disperse components of the skin care composition and more particularly aliphatic alcohols, esters, ethers, ketones, amines and hydrocarbons including the aromatic, nitrated and chlorinated hyrocarbons. Particularly preferred organic solvents are the lower aliphatic alcohols such as the $C_{1-3}$ alcohols and especially ethanol. Generally the solvent system will comprise from about 25 to 99.8% by weight of solvent, preferably 50 to 80%, from about 0.1 to 20% by weight of the starch derivatives, preferably 0.2 to 10%, from about 0.1 to 25% by weight of additives, preferably from about 0.1 to 15% and from about 0 to 75% by weight of propellant, preferably 0 to 35%.

The additives and other ingredients which may be included in either the aqueous or solvent based systems are the same as those described above for the emulsion and oil based systems. The propellants which may be included in the solvent system are the same as those described above for the aqueous systems. Additionally, a mixture of the aqueous and solvent systems may be used wherein water and solvent, especially alcohols are combined along with the components, i.e., starch derivative, additives and propellant. Such a composition will comprise 25 to 99.8% by weight of a combination of water and solvent, preferably 50 to 80% along with the components as described above.

Anhydrous and powdered systems may also be used incorporating the starch derivative of this invention. The anhydrous system will comprise as a base, materials such as mineral oil, wax, esters, volatile solvents, etc., and will also include the selected starch derivative, additives and active and functional ingredients. Powdered systems include powder materials such as talc, corn starch, and mica, fillers such as clay as well as other additives and active and functional ingredients. Generally the anhydrous system will comprise from about 10 to 99.8% preferably 10 to 90% by weight of base material, from about 0.1 to 65%, preferably 0.5 to 40% by weight of starch derivative and from about 0.1 to 25%, preferably 0.1 to 15% by weight of additives. The powdered system will comprise from 0 to 99.8%, preferably 1 to 90% by weight of the powder material, from about 0.1 to 99%, preferably 0.5 to 90% by weight of the starch derivative and from about 0.1 to 25%, preferably 0.1 to 15% by weight of additives.

The calcium salt starch devrivatives (I) used in cosmetic compositions in accordance with this invention will comprise an effective aesthetic enhancing additive amount. This can vary widely depending on the application. More particularly, the calcium salt starch derivative will comprise from about 0.1 to 99% and preferably from about 0.2 to 90% by weight, based on the weight of the composition. As noted earlier when using emulsion, aqueous and solvent systems the amount of calcium salt starch derivative will comprise from about 0.1 to 20% and preferably from about 0.2 to 10% by weight, based on the weight of the composition. When using anhydrous systems the amount of starch derivative will comprise from about 0.1 to 65% and preferably 0.5 to 40% by weight. When using powdered systems the amount of starch derivative will comprise from about 0.1 to 99% and preferably from about 0.5 to 90% by weight.

Preparation of the cosmetic emulsion compositions typically involves adding the oil soluble components in one vessel and heating to, e.g., 75° to 80° C. and combining the water soluble components in another vessel and heating to, e.g., 75° to 80°C. Depending on whether O/W or W/O emulsions are being prepared the warmed inner phase is then slowly added to the outer phase with agitation.

The following examples further illustrate the embodiments of this invention. In the examples all parts and percentages are given by weight and all temperatures are in degrees Celsius unless otherwise noted.

EXAMPLE I

A total of 1 kg of waxy maize starch was placed in a 4-liter blender and 2 liters of water added. The slurry was mixed at low speed until homogeneous and the pH adjusted to between 2-3 by adding hydrochloric acid. A total of 100g of the appropriate succinic anhydride (see table below) was added to the slurry with good agitation. The slurry was then placed in a stainless steel beaker in a constant temperature bath set at 35° C. and equipped with overhead motor and stirring paddle, pH electrode and dip tube for automatic addition of 3% aqueous sodium hydroxide. The automatic pH controller was set at 8.5 and allowed to react until consumption of caustic has stopped (i.e., less than 5 grams of caustic solution per hour). The reaction pH was adjusted to 5.5 with HCl and filtered. The resulting cake was washed with 2 L of water and resuspended into 2 L of fresh water followed by the addition of about 25 g of $CaCl_2$ and stirred for 1 hour. The slurry was filtered and washed (3×2 L) and allowed to air dry. The results are shown in Table 1.

TABLE 1

| Anhydride Reagent[1] | Treatment Level (%) | % Bound Reagent |
| --- | --- | --- |
| Decenyl | 10 | 5.8 |
| N-dodecenyl | 10 | 5.6 |
| Dodecenyl | 10 | 5.7 |
| Tetradecenyl | 10 | 5.4 |

[1] all reagents were substituted succinic anhydride

EXAMPLE II

The starch derivatives described in Example I plus others prepared in a similar manner were formulated into a cosmetic lotion having the following ingredients:

|  | Parts by Weight |
| --- | --- |
| Phase A |  |
| Cetyl Alcohol | 1.0 |
| Ceteth-20 | 1.0 |
| Glyceryl stearate | 1.0 |
| Stearic acid T.P. | 2.0 |
| $C_{12-15}$ alkyl benzoate | 5.0 |
| Octyl palmitate | 5.0 |
| Dimethicone copolyol | 1.0 |
| Phase B |  |
| Deionized water | 75.1 |
| Carbomer | 0.2 |
| Triethanolamine (99%) | 0.7 |
| Phase C |  |
| Propylene glycol | 3.0 |
| Experimental starch | 4.0 |
| Phase D |  |
| Germaben II E | 1.0 |

The carbomer of Phase B was dispersed in deionized water and heated to 80° C. followed by addition of triethanolamine. The ingredients of Phase A were combined and heated to 80°C.. Phase A was added to Phase B at a temperature of 80° C. and mixed for 10 minutes. The experimental starch of Phase C was slurried into propylene glycol and added to the cooled downed combination of Phases A/B (40°, 60°or 70° C. ). After the combined phases were cooled to 40°C. , Phase D was added followed by thorough mixing. Germaben II E, a product of Sutton Laboratories, is a combination of propylene glycol, diazolidinyl urea, methylparaben and propylparaben. The formulations were allowed to cool to room temperature and evaluated for heat stability. Hydrophobicity of the starch was determined by attempting to disperse the starch in water. Those not dispersing were considered hydrophobic and those dispersing were considered not hydrophobic. Results are shown in the following table.

TABLE 2

| | | Microscopic Evaluation[5] | | | | |
|---|---|---|---|---|---|---|
| | | Room | | | Room Temperature | |
| Sample[1] | Hydro-phobicity | Temperature[2] | 45° C. (oven)[2] | 60° C. (oven)[2] | 3 | 4 |
| Control | good | + | + | – | – | – |
| DSA | failed | not evaluated | not evaluated | | | |
| DSA (10%); CaCl$_2$ (2.5%) | good | + | +/– | – | +/– | – |
| DDSA (6%); CaCl$_2$ (2.5%) | good | + | + | +/– | + | +/– |
| TDSA (10%); CaCl$_2$ (2.5%) | good | + | + | + | + | + |
| OSA (8%); CaCl$_2$ (2.5%) | failed | +/– | +/– | – | – | – |

[1]Sample Description
Control - 2% octenylsuccinate with 2% aluminum sulfate
DSA - decenyl succinate anhydride
DDSA - dodecenyl succinic anhydride
TDSA - tetradecenyl succinic anhydride
OSA - octenyl succinic anhydride
[2]microscopic evaluation with starch sample incorporated at 40° C.
[3]microscopic evaluation with starch sample incorporated at 60° C.
[4]microscopic evaluation with starch sample incorporated at 70° C.
[5]result notation
+ = birefringence present after one month stability
+/– = partial birefringence present
– = birefringence absent

EXAMPLE III

A hand and body lotion containing the calcium salt starch derivative (dodecenyl) described in Example I was formulated and had the following ingredients:

| | Parts by Weight |
|---|---|
| Phase A | |
| Isopropyl palmitate | 3.00 |
| Hydrogenated polyisobutene | 2.00 |
| Stearic acid T.P. | 2.00 |
| Cetyl alcohol | 1.00 |
| Glyceryl stearate | 1.50 |
| Wheat germ oil | 0.75 |
| Sunflower seed oil | 0.75 |
| Jojoba oil | 0.75 |
| Squalane | 0.75 |
| Dimethicone | 0.25 |
| Phase B | |
| Deionized water | 70.10 |
| Triethanolamine | 0.50 |
| Potato starch (modified) | 2.00 |
| Aloe Vera gel 1:1 | 5.00 |
| Sodium laureth sulfate | 0.15 |
| Phase C | |
| Glycerine | 4.00 |
| Experimental starch | 4.00 |
| Tocopherol acetate | 0.25 |
| Retinyl palmitate | 0.25 |
| Germaben II E | 1.00 |
| | 100.00 |

Phase B ingredients were combined by adding the potato starch and triethanolamine with deionized water and heating to 80° C. and holding for 20 minutes followed by addition of the Aloe Vera gel and sodium laureth sulfate with mixing. The ingredients of Phase A were combined, heated to 80° C. and added to Phase B at 80° C. with mixing for 15 to 30 minutes. After cooling to 40°C., the experimental starch sample was combined with other Phase C ingredients, added to Phases A and B at 40° C. with mixing and then cooling to room temperature. This example shows the use of the calcium salt starch derivative as an effective additive in a lotion type composition.

EXAMPLE IV

A treatment body cream containing the starch derivative (dodecenyl) as described in Example I was formulated and had the following ingredients:

| | Parts by Weight |
|---|---|
| Phase A | |
| Caprylic/capric triglyceride | 6.00 |
| C$_{12-13}$ alkyl benzoate | 4.00 |
| Isocetyl stearate/isocetyl alcohol | 2.00 |
| Cetearyl alcohol | 2.00 |
| Stearic acid T.P. | 1.00 |
| Glyceyl stearate SE | 1.50 |
| Dimethicone | 0.50 |
| Cetyl acetate/acetylated lanolin alcohol | 1.00 |
| Kukui nut oil | 1.50 |
| Macadamia nut oil | 1.00 |
| Phase B | |
| Deionized water | 66.35 |
| Triethanolamine | 0.30 |
| Potato starch (modified) | 2.00 |
| Methylparaben | 0.20 |
| Propylparaben | 0.15 |
| Na$_3$ EDTA | 0.05 |
| Butylated hydroxyanisole | 0.05 |
| Phase C | |
| Propylene glycol | 4.00 |
| Experimental starch | 4.00 |
| Tocopheryl acetate | 0.30 |
| Butylene glycol/water/Hops Extract | 0.50 |
| Butylene glycol/water/Horse Chestnut Extract | 0.75 |
| Butylene glycol/water/Kiwi Extract | 0.50 |
| Phase D | |
| Imidazolidinyl urea | 0.35 |
| | 100.00 |

Phase B ingredients were combined and heated to 80° C. and held for 20 minutes. Phase A ingredients were combined and heated to 80° C. and then added to Phase B at 80° C. and mixed for 10 minutes. After cooling to 40° C., the A/B combination was added to Phase C and mixed and then Phase D added, mixed and cooled to room temperature. This example shows the use of the starch derivatives of this invention in a cream type composition which provides good aesthetic and feel characteristics on skin.

EXAMPLE V

A cream to powder eye shadow composition containing the starch derivative (dodecenyl) described in Example I was formulated and had the following ingredients.

| | Parts by Weight |
|---|---|
| Phase A | |
| Octyl dodecanol | 13.00 |
| Acrylates/octylacrylamide copolymer | 1.00 |

-continued

| | Parts by Weight |
|---|---|
| Phase B | |
| Microcrystalline wax | 0.30 |
| Cyclomethicone/quaternium -18 Hectorite/propyline carbonate | 30.00 |
| Phase C | |
| Caprylic/capric triglycerides | 3.00 |
| Octyl dodecyl stearate | 0.50 |
| Triglycerol diisostearate | 4.00 |
| Tocapherol acetate | 0.10 |
| $C_{11-12}$ isoparaffin | 7.40 |
| Silica silylate | 0.50 |
| Mica/iron oxide/titanium dioxide | 10.00 |
| Experimental starch | 30.00 |
| Phenoxyethanol | 0.20 |
| | 100.00 |

The ingredients of Phase A were slowly combined and heated to 80° C. with mixing. Phase B was added and then Phase C added with thorough mixing and then cooled to room temperature. This example shows the addition of the starch derivative of this invention to an anhydrous type formulation.

EXAMPLE VI

A pressed translucent face powder containing the starch derivative (dodecenyl) described in Example I was formulated and had the following ingredients:

| | Parts by Weight |
|---|---|
| Phase A | |
| Experimental starch | 79.78 |
| Corn starch | 7.70 |
| Barium sulfate | 0.30 |
| Propylparaben | 0.10 |
| Methylparaben | 0.10 |
| Titanium dioxide | 6.50 |
| Mica | 2.00 |
| Brown iron oxide | 0.75 |
| Red iron oxide | 0.25 |
| Transparent yellow iron oxide | 0.02 |
| Phase B | |
| Isoeicosane | 2.50 |
| | 100.00 |

Phase A ingredients were mixed together until uniform. Phase B was sprayed onto Phase A and blended together until uniform and then pressed.

EXAMPLE VII

A topical spray powder containing the calcium salt starch derivative (dodecenyl) described in Example I was formulated and had the following ingredients:

| Ingredients | Parts by Weight |
|---|---|
| Anhydrous ethanol | 42.00 |
| Aminomethyl propanol 95% | 0.38 |
| Acrylates/octylacrylamide copolymer | 2.00 |

| Ingredients | Parts by Weight |
|---|---|
| Experimental starch | 10.00 |
| Isobutane propellant | 45.62 |
| | 100.00 |

The aminomethyl propanol was dissolved in ethanol and while maintaining good agitation slowly adding the acrylate/octylacrylamide copolymer. When the solution addition is complete the starch sample was added and mixed well until homogeneous. The example shows the suitable addition of the starch derivatives of this invention in a spray powder type formulation

What is claimed is:

1. A cosmetic skin care composition having hydrophobic properties and good heat stability and comprising a cosmetic vehicle and from about 0.1 to 99% by weight of a calcium salt derivative having the following formula:

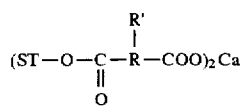

wherein ST is starch. R is dimethylene. R' is an alkenyl group having 10 to 16 carbon atoms and wherein from about 3 to 25% by weight of the

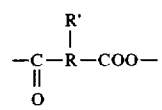

group is bound to the starch. based on the weight of dry starch.

2. The composition of claim 1 wherein R' has 12 to 14 carbon atoms.

3. The composition of claim 1 which contains from about 3.5 to 10% by weight of the bound group.

4. The composition of claim 1 wherein cosmetic vehicle is an emulsion, an aqueous system, a solvent system. a mixture of aqueous and solvent systems, an anhydrous system of a powdered system.

5. The composition of claim 4 wherein R' has 12 to 14 carbon atoms.

6. The composition of claim 4 which has from about 3.5 to 10% by weight of the bound group.

7. The composition of claim 1 wherein from about 0.1 to 20% by weight of the starch derivative is used based on the weight of cosmetic composition.

8. The composition of claim 7 wherein R' is an alkenyl group having 12 to 14 carbon atoms and there is from about 3.5 to 10% by weight of the bound group.

9. A cream or lotion composition having the composition of claim 1 wherein the cosmetic vehicle is an emulsion and from about 0.1 to 20% by weight of the the starch derivative is used based on the weight of cosmetic composition.

10. The composition of claim 9 wherein R' is an alkenyl group having 12 to 14 carbon atoms.

11. The composition of claim 10 wherein from about 0.1 to 10% by weight of the starch derivative is used and there is from about 3.5 to 10% by weight of the
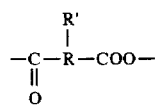
group is bound to the starch, based on the weight of dry starch.
12. The composition of claim 11 wherein the starch is waxy maize and has from about 4 to 6% by weight of the bound group based on the weigh of dry starch.
* * * * *